United States Patent [19]
Alcock et al.

[11] Patent Number: 5,556,534
[45] Date of Patent: Sep. 17, 1996

[54] ELECTROCHEMICAL OXYGEN AND PH SENSORS EMPLOYING FLUORIDE BASED SOLID-STATE ELECTROLYTES

[75] Inventors: Charles B. Alcock, Toronto, Canada; Nikesh Bakshi, South Bend, Ind.

[73] Assignee: The University of Notre Dame, Notre Dame, Ind.

[21] Appl. No.: 404,473

[22] Filed: Mar. 14, 1995

[51] Int. Cl.$^6$ .................................................. G01N 27/26
[52] U.S. Cl. .................. 205/787.5; 205/782; 205/782.5; 205/783.5; 205/784; 204/421; 204/433; 204/435; 204/416; 204/404
[58] Field of Search .................................... 204/421, 433, 204/435, 416, 404, 153.21, 153.16, 153.18

[56] References Cited

U.S. PATENT DOCUMENTS

| | | | |
|---|---|---|---|
| 4,479,867 | 10/1984 | Siebert et al. | 204/421 |
| 4,864,462 | 9/1989 | Madou et al. | 361/280 |
| 5,133,857 | 7/1992 | Alberti et al. | 204/421 |
| 5,134,042 | 7/1992 | Madou et al. | 204/426 |
| 5,256,272 | 10/1993 | Alcock et al. | 204/421 |

OTHER PUBLICATIONS

Alcock et al., "New Electrochemical Sensors for Oxygen Determination," Solid State Ionics (1992), 53–56:39–43. No month available.

Nagel et al., Fast Ion Transport in Solids (W. Van Goal ed., North Holland, Amsterdam (1973), 165–170. No month available.

Alcock et al., "A Fluoride–Based Composite Electrolyte", Solid State Ionics (1990), 39:245–249. No month available.

Kuwata et al., "Response of a Solid–State Potentiometric Sensor Using LaF$_3$ to a Small Amount of H$_2$ or CO In Air at Lower Temperatures", Chemistry Letters (1984), 1295–1296. No month available.

Mingmei and Yufang, "A New Hydrogen Sensor With Rare Earth Complex Flouride", Sensors and Actuators B.S., (1992), 179–180. No month available.

*Primary Examiner*—Bruce F. Bell
*Attorney, Agent, or Firm*—Flehr, Hohbach, Test, Albritton & Herbert

[57] ABSTRACT

Electrochemical sensors and methods for their use are provided for the detection of the pH and/or oxygen concentration in an aqueous medium. The subject sensors comprise a closed-end cylinder shaped fluoride based solid-state electrolyte having an inner and outer surface. In contact with the inner surface of the electrolyte is a solid reference electrode. In a preferred embodiment, the electrolyte is described by the formula $La_{0.95}X_{0.05}F_{2.95}$, wherein X is an alkaline earth metal. In addition to finding use in the detection of the pH or oxygen concentration of a medium where one these factors is known, at least two of the subject sensors may be used in conjunction, where the reference electrode differs between the two sensors, to determine the pH and oxygen concentration of a medium where both of these values are unknown.

18 Claims, 4 Drawing Sheets

ELECTROCHEMICAL OXYGEN AND PH SENSORS EMPLOYING FLUORIDE BASED SOLID-STATE ELECTROLYTES

TECHNICAL FIELD

The technical field of this invention is electrochemical oxygen and pH sensors.

BACKGROUND

There are many situations where it is desirable to be able to monitor the pH and/or oxygen concentration of an aqueous medium. For example, in power generating facilities employing aqueous cooling systems, corrosion continues to be a problem. Corrosion refers to the loss or conversion into another insoluble compound of a solid in contact with a liquid, e.g. pipes in contact with water of a coolant system. Corrosion can result in significant economic costs. For example, corrosion can weaken the physical strength and integrity of pipes, thereby necessitating their replacement. Furthermore, corrosion can pose significant safety risks, as corroded material is more likely to break. Two factors that contribute to the corrosion potential of an aqueous medium are the oxygen concentration and pH of the medium.

In order to counteract the effects of corrosion, sensors have been developed which can monitor the oxygen concentration and pH of the system. If the value of either the oxygen concentration or pH varies from a value associated with a low corrosion potential, measures can be taken to return the oxygen concentration or pH to a more desirable value, e.g. by addition of NaOH if the pH becomes too acidic.

Typically the oxygen concentration and pH of water in a cooling system have been monitored by taking a sample of water from the system in what is known as a "grab sample basis." However, in this type of monitoring, the sample tested is not at the same temperature as the sample in the system. Because the emf of an electrochemical sensor is affected by the temperature of the medium being tested, in such methods one does not obtain an emf from which the true pH or oxygen concentration of the medium can be derived.

To address the problems of monitoring on a "grab sample basis," sensors have been developed for monitoring the oxygen concentration and pH of an aqueous medium in situ. For temperatures exceeding 350° C., yttria or calcia stabilized zirconia solid-state electrolyte sensors have found use. However, these sensors are not suitable for use in temperatures below 350° C. because of the poor conductivity of the electrolyte at these lower temperatures. Likewise, glass electrodes have been found suitable for use with aqueous mediums at ambient temperature. However, these sensors fail at higher temperatures due to degradation of the glass membranes. Thus, the opportunity to monitor the oxygen concentration and pH of an aqueous medium in situ at temperatures between about 25° and 350° C. has remained limited, if not non-existent.

Accordingly, there is continued interest in the development of sensors which can be used in situ to monitor the oxygen concentration and pH in aqueous mediums with temperatures ranging from 25° to 350° C. Such sensors should be physically and chemically inert in the working environment of the coolant system in which they are employed, e.g. the temperature and pressure range of the aqueous medium to be tested. Furthermore, such sensors should be able to provide an accurate reading in a relatively short period of time, so that deviations in the corrosion potential of the aqueous medium can be quickly remedied.

RELEVANT LITERATURE

For a general review of corrosion, see Brett & Brett, Electrochemistry, Principles, Methods and Applications (Oxford University Press, 1993) pp 352 to 356.

Monitoring of pH and oxygen concentration in aqueous coolant systems is discussed in: "Monitoring Techniques for pH, Hydrogen and Redox Potential in Nuclear Reactor Circuits," Palo Alto, Calif.: Electric Power Research Institute, January 1983, NP-2806; "Measurement of pH and Corrosion Potentials of Tube Alloys in Solutions Found in Steam Generators," Palo Alto, Calif.: Electric Power Research Institute, (May 1987) NP-5193.

Fluoride based solid state electrolytes are discussed in: Alcock & Li, "A Fluoride-Based Composite Electrolyte," Solid State Ionics (1990) 245–249; Alcock et al., "New Electrochemical Sensors for Oxygen Determination," Solid State Ionics (1992) 53–56.

SUMMARY OF THE INVENTION

Electrochemical sensors containing fluoride based, solid state electrolytes are provided for the in situ detection of the oxygen concentration and/or pH of an aqueous medium. In a preferred embodiment, the subject electrolyte is described by the formula $La_{0.95}X_{0.05}F_{2.95}$, where X is an alkaline earth metal. The electrolyte may optionally be doped with an oxide. The subject electrolyte is in the form of cylinder closed at one end. Inside the closed-end cylinder is a solid reference electrode. In using the subject sensors, the outer surface of the electrolyte cylinder is contacted with an aqueous medium. By measuring the resultant emf across the electrolyte, the oxygen concentration and/or pH of the aqueous medium in contact with the outer surface of the electrolyte may be derived. By using two of the subject sensors, where each sensor differs with respect to the internal reference electrode, one may detect both the pH and oxygen concentration of an aqueous medium where both values are unknown.

DESCRIPTION OF THE SPECIFIC EMBODIMENTS

Figure 1:
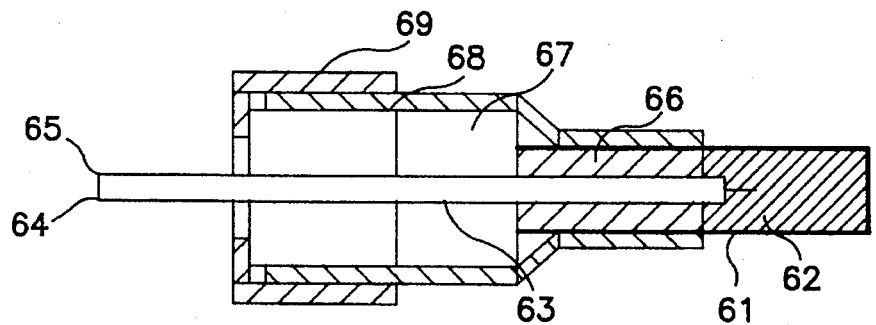
FIG. 1 is a sectional view of a sensor assembly according to the subject invention.

Electrochemical sensors containing fluoride based solid state electrolytes, and methods of their use, are provided for the in situ detection of the oxygen concentration and/or pH of an aqueous medium. In a preferred embodiment of the invention, the electrolyte of the subject sensors is in the form of a cylinder that is closed at one end. Inside the closed-end cylinder is a solid internal reference electrode. In using the subject sensors, the outer surface of the electrolyte is contacted with the aqueous medium to be tested, the resultant emf across the electrolyte is measured and the pH and/or oxygen concentration of the aqueous medium is derived from the measured emf. By employing two of the subject sensors in conjunction, where the two sensors differ with respect to the internal reference electrode, the pH and the oxygen concentration of the aqueous medium may be determined where both values in the contacted medium are unknown.

The fluoride based solid-state electrolytes of the subject invention may be any fluoride based solid-state electrolyte which is physically and chemically inert, i.e. stable, in the working environment (described below) in which the sensor is employed. The electrolyte should be a pure ionic conductor and have a high conductivity in the working environment. Furthermore, the electrolyte should be one in which stable emfs are generated in a relatively short period of time, usually in less than about 20 min, more usually in less than about 10 min and preferably in less than about 5 min. Fluoride based electrolytes that find use include $LaF_3$, $CeF_3$, $CaF_2$, $BaF_2$ and the like. See Nagel and O'Keefe, "Highly Conducting Fluorides Related to Fluoride and Tysonite," in Fast Ion Transport in Solids (ed. W.Van Cool, North Holland, Amsterdam) (1973) p 165 which provides a guide to various fluorides and their conductivities at various temperatures.

Preferred fluoride based solid-state electrolytes may be described by the formula:

$$La_\alpha X_\beta F_\lambda$$

where a ranges from 0.95 to 1.0, and is usually about 0.95

X is an alkaline earth metal selected from group consisting of Ba, Sr, Ca and the like, $\beta$ ranges from 0.0 to 0.05, and is usually about 0.05 and $\lambda$ ranges from 2.95 to 3.0, and is usually about 2.95.

The electrolyte may further be doped with an oxide, especially where the sensor is designed to detect the oxygen concentration of an aqueous medium. The dopant oxide will be an oxide of one of the consituent fluorides in the electrolyte and should be chemically stable. For example BaO, SrO and $La_2O_3$ find use as the dopant oxide because of their chemical stability but CaO is less preferred since CaO reacts with atomspheric moisture to form hydroxide. Any suitable doping oxide may be employed, where the oxide will comprise from about 2 to 8% of the total electrolyte composition, and will usually be about 5% of the total electrolyte composition. Oxides which find use include $La_2O_3$, BaO, SrO and the like. For hydrogen sensors, the electrolyte may or may not be doped with a doping oxide, and will preferably not be doped with an oxide.

The subject electrolytes will be fabricated to have a first major surface and a second major surface, where the first major surface is in contact with the aqueous medium to be tested and the second major surface is in contact with the internal reference electrode. In preferred embodiments, the subject electrolytes will be fabricated into a shape having an inner surface (serving as the second major surface) and an outer surface (serving as the first major surface), where the volume defined by the inner surface is capable of containing a solid reference electrode. Any suitable shape may be employed, but a preferred shape is a cylinder sealed at one end, inside of which the reference electrode may be placed. In fabricating the subject electrolytes, any convenient method may be employed. One method that finds use is the slip-casting method described by Pelton et al., U.S. Pat. No. 4,338,272, the disclosure of which is herein incorporated by reference. In the method described by Pelton, the electrolyte consituents are ground into a fine particle mixture and supended in an organic solvent. The suspension is then poured into a mold that absorbs the solvent, leaving the layer of electrolyte consituent powder on the wall. After the deposited tube has reached the desired thickness, the tube is dried and then removed from the mold. The tube is then sintered, resulting in a dense, solid-state electrolyte tube.

Any convenient reference electrode may be employed in the subject sensors. Because of the working environment in which the sensors are designed to operate, solid reference electrodes are preferred. Reference electrodes which can generate a fixed chemical potential in the working environment may be employed. The particular reference electrode selected should be able to attain equilibrium in a suitably short period of time, usually in less than 20 min, more usually in less than 10 min and preferably in less than 5 min. Reference electrodes which find use include metal/metal oxide electrodes, e.g. $Cu/Cu_2O$ and metal oxide (I)/metal oxide (II) electrodes, e.g. $Cu_2O/CuO$; and metal/metal hydride electrodes, e.g. $Zr/ZrH_2$, $Ti/TiH_2$ and the like. Of particular interest are the solid metal/metal oxide reference electrodes $Ag/Ag_2O$ and $Hg/HgO$, as well as the solid hydride reference electrode $Ti/TiH_2$.

In using the subject sensors to measure the pH and/or oxygen concentration of an aqueous medium, the subject sensors will be used with electrical leads by which the emf across the electrolyte between the inner and outer surface of the electrolyte may be measured. One lead will electrically connect the internal reference electrode with a means for measuring the emf across the electrolyte, while a second lead will electrically connect the outer surface of the electrolyte with the same emf measurement means. The leads may be made of the same or different material, as long as the material is a conducting material. Typically, the leads will be a metal, such as Ag, Pt, chromel and the like. To improve the electrical contact between the outer surface of the electrolyte and the lead, a porous conducting material may be coated on the outer surface of the electrolyte. Any conducting material may be employed, so long as it does not interfere with the contact of the electrolyte outer surface with the species being measured in the aqueous medium. Suitable materials include metal alloy films, e.g. sputtered Au/Pd films, pastes, e.g. Pt pastes and the like. In viewing the subject sensors as electrochemical cells comprising a reference and working electrode separated by an electrolyte, it is convenient to think of the outer surface of the electrolyte and medium with which it is contacted as the working electrode, where the activity of the species being measured at this working electrode is measured by the electrical lead in contact with the outer surface of the electrolyte.

The sensor of the device having been described in general terms, a representative sensor according to the subject invention will now be discussed in greater detail with respect to FIG. 1. High density fluoride electrolyte tube 61 is packed with the reference electrode 62. A double bore alumina ceramic tube 63 containing chromel 64 and aluminel 65 wires was inserted inside the sensor tube, in contact with the reference electrode. The chromel wire serves as the contact wire. The double barrel ceramic tube is set in place with a high temperature epoxy 66. The epoxy serves as a sealant to prevent the contact of atmospheric air with the reference electrode inside the electrolyte tube. A Teflon® seal 67 inside a steel fitting 68 fixes the fluoride tube sensor. When the nut 69 is tightened, a leak proof seal results.

Figure 5:
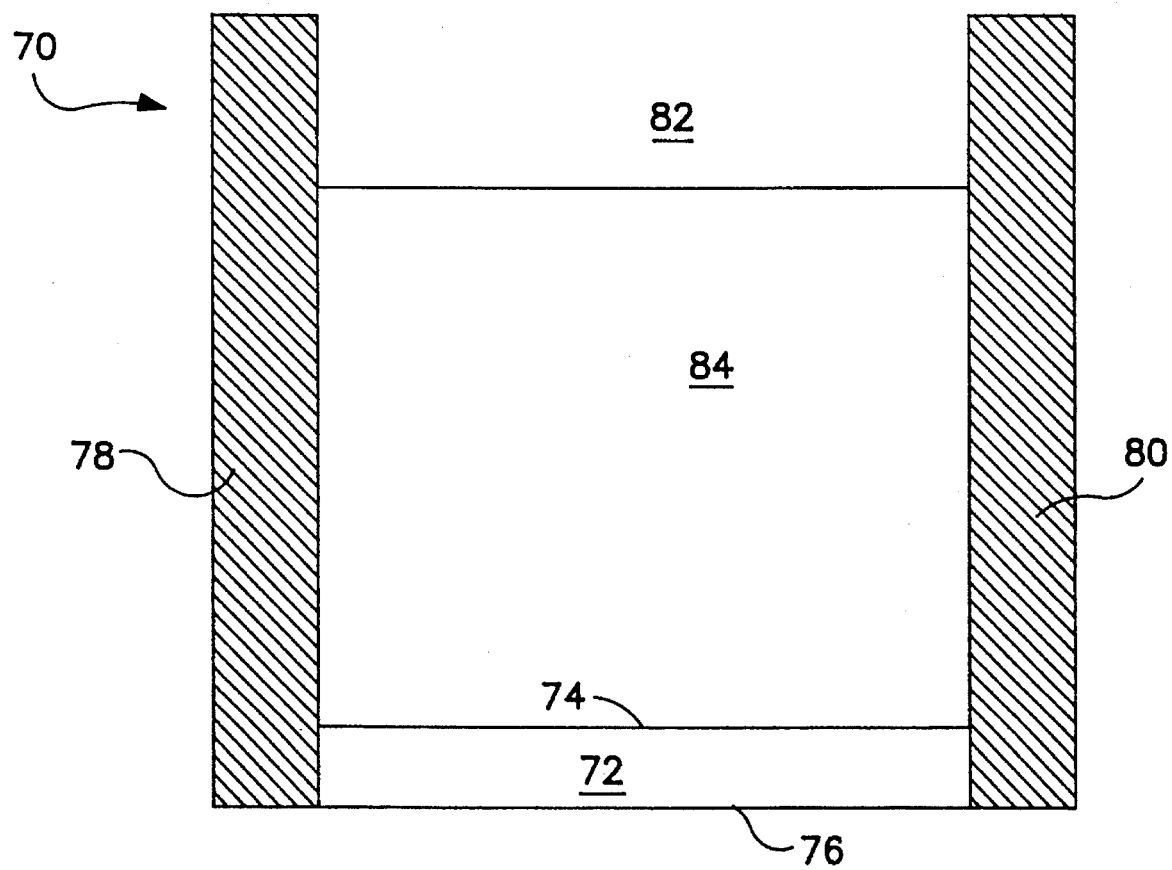
FIG. 5 is a sectional view of an alternative embodiment of the sensor assembly according to the subject invention.

An alternative embodiment of the subject sensors is shown in FIG. 5. Sensor 70 comprises electrolyte 72 having a second major surface 74 and a first major surface 76. Walls 78 & 80 are made of a suitably inert material to the working environment and complete volume 82 inside of which is solid reference electrode 84 which is in electrical contact with second major surface 74. In using the sensor, contact wires (not shown) are used to measure the potential across the solid electrolyte between the first and second major surfaces.

Sensors based on the subject fluoride based solid state electrolyte can be used to detect both the oxygen concentration and pH of an aqueous medium. Since the subject sensors include fluoride based solid-state electrolytes, they are sensitive to both the pH and the dissolved oxygen concentration of the medium in which they are in contact.

The subject sensors may be used in a wide range of working environments, where the term working environment is used to refer to the various physical and chemical characteristics of the medium to be tested. Mediums that may be tested with the subject sensors are typically aqueous. The temperature of the aqueous test medium may range from 25° to 350° C. and will usually range from 50° to 350° C. The pressure of the aqueous medium may range from 100 to 1000 psi and will usually be from 300 to 400 psi. The subject sensors are particularly suited for in situ measuring of the pH and oxygen concentration of an aqueous medium in a coolant system.

In using the subject sensors, the outer surface of the electrolyte is contacted with the aqueous medium to be tested. The outer surface of the electrolyte will be in contact with the aqueous medium for at least a sufficient period of time for a stable emf to be generated across the electrolyte, e.g. for the sensor to reach equilibrium. Factors in the medium which influence the time required to achieve a stable emf include volume of medium being tested, temperature of the medium, oxygen concentration and the like. The sensor will be contacted with the aqueous medium for at least about 15 min, more usually for at least about 30 min, and may be contacted with the aqueous medium for longer periods of time, such as hours, days or weeks to provide for continuous on-line monitoring of the pH and/or oxygen concentration of the aqueous medium.

Since the subject sensors are sensitive to both pH and oxygen in an aqueous medium, if the value of one of these factors is known for the aqueous medium, then the sensor may be used to determine the other, unknown value. For example, for measurement of the pH of an aqueous medium using the subject sensors, if the oxygen concentration of the aqueous medium is known, one can derive the unknown pH of the medium from the observed emf.

Because the subject sensors are sensitive to both the pH and the oxygen concentration of the aqueous medium, the subject sensors may be employed to determine these values in an aqueous medium where they are both unknown. To detect both the pH and oxygen concentration of an aqueous medium where both values are unknown, at least two, usually two, sensors are contacted with the medium in conjunction and the resultant emf across the electrolyte of each sensor is measured at substantially the same time, preferably simultaneously. Any combination of sensors may be employed as long as the sensors differ with respect to their internal reference electrodes. In a preferred embodiment of the subject method, one of the sensors will have an oxide internal reference electrode while the other will have a hydride internal reference electrode. The sensors will be contacted with the medium at any position relative to one another as long as they are not touching and the working environment of each sensor is the same, e.g. 1 cm apart. Although the above method has been described in terms of using two distinct sensors, a hybrid or double-headed sensor in which a first head comprises a first reference electrode and a second head comprises a different reference electrode may be employed.

After sufficient time has elapsed for a stable emf to be generated across the electrolyte of each sensor, the emfs from each sensor will be measured. Usually the emfs will be measured at least 15 min after contact, and more usually at least 30 min after contact. By knowing the relationship of the emf of each sensor to the oxygen concentration, pH and temperature of the contacted medium, one may obtain the pH and oxygen concentration of the medium where these values are previously unknown. Using the observed emfs from the two sensors, an algorithm or logic means is used to derive the unique pH and oxygen concentration of the medium. Any suitable algorithm may be employed, where the algorithm may be conveniently solved with a computer means. The two emfs can be measured continuously and fed into a computer through an I/O device. After the calculation using the algorithm, oxygen concentration and pH can be displayed continuously. Furthermore, the computer can be used in conjunction with a means to automatically adjust the pH/oxygen concentration of the aqueous medium when the pH/oxygen concentration deviates from the optimum value.

The following experiments are offered by way of illustration and not by way of limitation.

EXPERIMENTAL

1. Preparation of Solid State Fluoride Based Electrolytes for Use in Oxygen and pH Sensors The closed-end cylinder shaped fluoride based solid-state electrolytes used for the sensors described below were prepared as described in U.S. Pat. No. 4,338,272, the disclosure of which is herein incorporated by reference. See also Rivier and Pelton, Ceramics Bulletin (1978) 57:153.

Sensors having the general formula:

reference electrode|solid electrolyte|working electrode were prepared from the above electrolytes for detection of both pH and oxygen concentration in aqueous mediums as shown in Examples 2 through 6.

The conductivity of these solid electrolytes was found to be 4 to 5 orders of magnitude higher than that of stabilized zirconia. The electrolyte was found to be chemically and structurally stable in water up to 250° C. Finally, stable emfs are quickly established with these sensors at fixed temperatures, where the emf of the sensors responds in Nernstian fashion with the oxygen chemical potential in the water.

Example 2. Preparation and Characterization of Sensors

Figure 2:
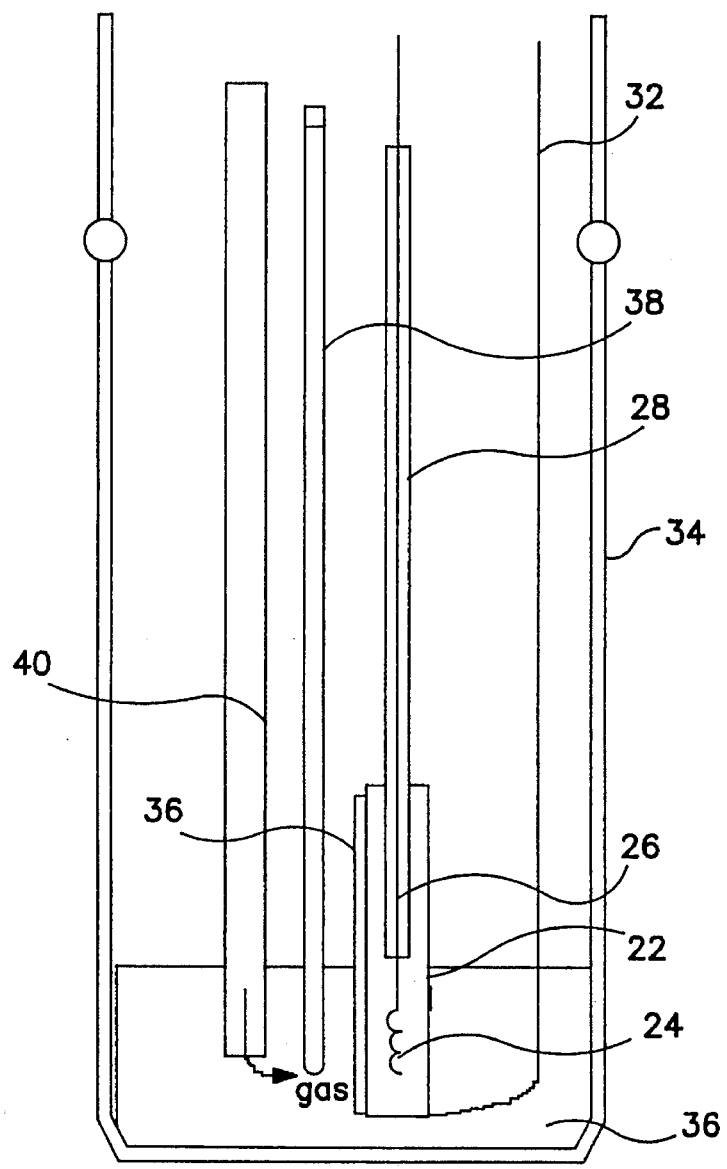
FIG. 2 provides a representation of the experimental set up used to test sensors according to the subject invention.

Three different sensors for measuring oxygen concentration in an aqueous medium over a temperature range of 50° to 250° C. were prepared. Each sensor was based on the following electrochemical cell configuration:

Pt, Ref. Electrode*$|La_{0.95}Ba_{0.05}F_{2.95}$+5 mole % $La_2O_3|H_2O$ (O$_2$+Ar),Pt*where the Ref. Electrode was either:

(a) water equilibrated with a fixed oxygen partial pressure (b) Hg/HgO (c) Ag/Ag$_2$O The sensors based on the above electrochemical cell with electrolytes as prepared in Example 1 were constructed and tested in the experimental configuration shown in FIG. 2. The closed end cylinder shaped solid electrolyte 22 contains the reference electrode 24. A silver wire 26 connects reference electrode 24 with a means for measuring emf (not shown). Silver wire 26 is housed in alumina tube 28. Since the temperature did not exceed 100° C., any contribution to the observed results due to dissimilar metals was negligible. On the outer surface of electrolyte cylinder 22 is platinum paste 30. Platinum wire 32 electrically connects the outer surface of the electrolyte with the means for measuring emf. A glass tube 34 contains an aqueous medium to be tested 36. The electrolyte sensor comprising elements 22–32 extends into medium 36 so that the outer surface of the electrolyte tube is in contact with the medium. Thermocouple 38 is used to monitor the temperature of medium 36. Gas is introduced into the aquous medium 36 by gas delivery tube 40.

To characterize each of the above sensors for their suitability as oxygen sensors, the observed emf for each sensor design in response to varying concentrations of oxygen in the aqueous medium 36 was measured. Where the temperature was held constant at 67° C. and the pH was constant, the observed emf across the electrolyte was found to vary linearly from approximately –330 mV to –280 mV with the log ($P_{O_2}$) over a range of –1.2 to 0.0.

The sensor based on the electrochemical cell:

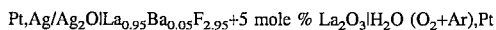

Pt,Ag/Ag$_2$O|La$_{0.95}$Ba$_{0.05}$F$_{2.95}$+5 mole % La$_2$O$_3$|H$_2$O (O$_2$+Ar),Pt was further characterized at temperatures ranging from 100° to 247° C.

It was found that over this temperature range, stable emfs were obtained at fixed temperatures and oxygen partial pressures with the above sensor. When the oxygen partial pressure of the aqueous medium 36 was changed from one value to another, the emf changed accordingly to another stable value. When the oxygen partial pressure was returned to its original value, the emf also returned to its original value. The time to achieve a stable emf for the change from higher oxygen pressure (air or pure oxygen) to lower oxygen pressure was longer than that from lower oxygen pressure to higher oxygen pressure. Over a period of several days at 237° C. and 54.4 atm, the observed emf remained stable.

The above results demonstrate that sensors comprising the fluoride based, solid-state electrolytes as prepared in Example 1 can be used to detect the oxygen concentration in an aqueous medium over a temperature ranging from 50° to 250° C.

The response of sensors based on the solid state electrolytes of Example 1 to changes in pH of an aqueous medium was also studied. Two different sensors were constructed based on the following electrochemical cells:

(I) Pt, Ag/Ag$_2$O|La$_{0.95}$Ba$_{0.05}$F$_{2.95}$+5 mole % La$_2$O$_3$|pH buffer, Au/Pd,Pt (II) Pt, Hg/HgO|La$_{0.95}$Ba$_{0.05}$F$_{2.95}$+5 mole % La$_2$O$_3$|pH buffer, Au/Pd, Pt In mediums where the temperature exceeded 100° C., a platinum paste was employed instead of an Au/Pd film The sensitivity of the cell to pH was measured by observing the emf which results across the electrolyte for buffers having different pH values in the working electrode. For pH buffers of 4, 7, 9 and 10, buffers were obtained from Fisher Scientific Company. Buffer solution of pH 4 was 0.05 molar potassium biphthalate solution containing 0.05% formalin. Buffer solutions of pH 9 and 10 were solutions of boric acid-potassium chloride-sodium hydroxide. pH 7 buffer was a 0.05 molar solution of potassium phosphate and monobasic sodium hydroxide. Highly acidic buffers were prepared as follows: 0 (1M HCl), 1 (0.1M HCl), 2 (0.01M HCl). The pH of each of the solutions was confirmed by use of a pH/ion meter sold under the name of Accumet® by Fisher Scientific.

To study the correspondence of observed emf with changing pH in sensor I, sensor I was contacted with pure water and a stable emf of –350 mV was observed. After 40 min., 10 ml of saturated NaOH was then added to the water causing a sudden drop in the observed emf, which stabilized after approximately 5 min. to –750 mV. 20 ml of concentrated HCl (about 37% w/w) was then added to the solution, which roughly neutralized the NaOH, thereby returning the pH to roughly the same value of the pure water at the beginning of the experiment. The emf returned to the originally observed emf of –350 mV in a period of less than 5 min.

The reversibility of the sensor after temperature variation was checked by randomly changing temperatures. The sensor showed good reproducibility of emf throughout the temperature cycle (57° to 97° C.). The emf of the cell at steady pH varied linearly with the temperature over a range from 57° to 97° C. The emf of the sensor varied linearly with the pH over a pH range of 7 to 10.5. The results were reproducible.

Similar results were observed for sensor II above.

The above results demonstrate that the Sensors I and II can be used as sensors to detect the pH in aqueous mediums in which the oxygen concentration is held constant.

2. Determination of Both pH and Oxygen Concentration in Aqueous Mediums

As shown in experiments 1 and 2 above, a sensor based on the cell:

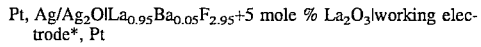

Pt, Ag/Ag$_2$O|La$_{0.95}$Ba$_{0.05}$F$_{2.95}$+5 mole % La$_2$O$_3$|working electrode*, Pt

*either H$_2$O (O$_2$+Ar) or pH buffer
provides an emf which varies linearly with: (a) pH at a fixed oxygen concentration and (b) with the oxygen concentration at a fixed pH, i.e. the sensor behaves in a Nernstian fashion with respect to both oxygen concentration and pH. Thus, both the oxygen partial pressure and pH of the aqueous medium in contact with the outer surface of the electrolyte contribute to the observed emf across the electrolyte. In order to characterize the contribution of the oxygen concentration and pH to the observed emf of this sensor, the cell emf was measured at oxygen partial pressures ranging from 0.09–0.91 at pH 7, 8 and 9. All of the measurements were made at 66° C. Based on the observed results, by combining both the oxygen partial pressure and pH contribution together at 66° C., the cell emf for this sensor at 66° C. can be expressed as:

Emf(mV)=39.37+52.62log$P_{O_2}$–47.4 pH ($P_{O_2}$=0.09–0.91, pH=7–9)

With the above characterization, it is possible to use this sensor to determine the pH or the oxygen concentration in an aqueous medium, where both values are unknown. To measure both values, the above sensor is used in conjunction with a sensor that is sensitive solely to pH or oxygen concentration, e.g. a glass electrode sensor for pH. One need only take the pH measured from the pH sensor and enter the value into the above equation and, knowing the emf, solve for log $P_{O_2}$ and thereby obtain the oxygen concentration of the contacted medium.

4. The Relationship of EMF to Temperature, pH and $P_{O_2}$ in Various Sensor Configurations at Temperatures in Excess of 100° C.

Figure 3:
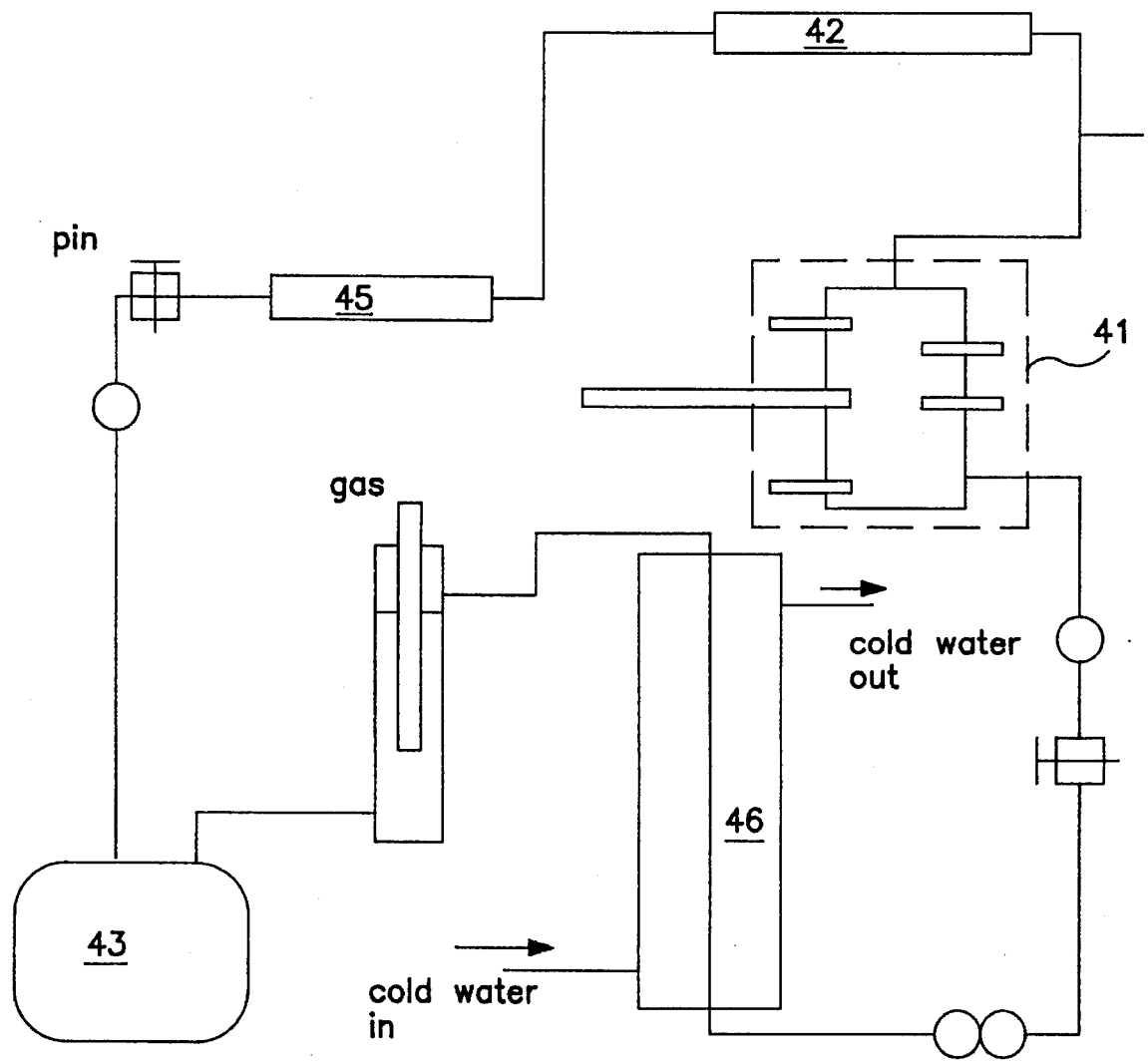
FIG. 3 provides a schematic representation of a system used to study the electrochemical response of sensors according to the subject invention with response to variations in pH and oxygen concentration in an aqueous medium which is at high temperature and pressure.

To determine the relationship of the observed emf of a sensor comprising the subject fluoride based solid electrolytes to temperature, pH and $P_{O_2}$ at temperatures in excess of 100° C., the sensor was studied in the system represented schematically in FIG. 3. In the system, fluid optionally entered the sensor chamber 41 from a preheater 42. The pressure in the solution was maintained with metering pump 43. Vibrations from the metering pump were reduced by including a dampener 45 in the flow loop. The cooling tower 46 ensured that temperature entering the pump did not exceed 60° C. The emf from each sensor in the sensor chamber was measured with a Keithley 199 DMM (Digital Multimeter) with an 8 channel scanner (not shown).

Figure 4:
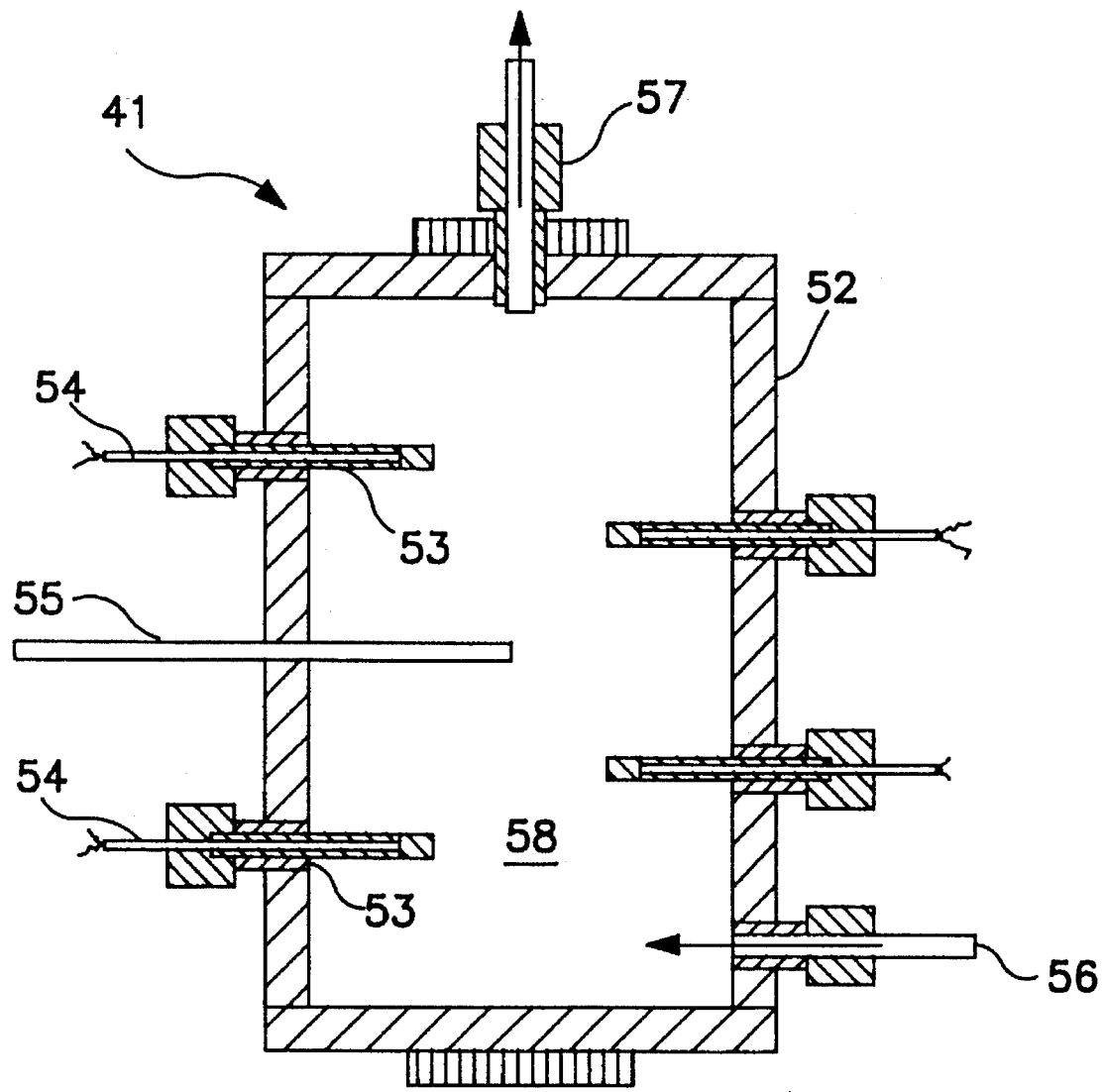
FIG. 4 is an enlarged view of the sensor chamber of the system represented by FIG. 3.

The sensor chamber 41, shown in FIG. 4, consisted of a stainless steel vessel 52 with a wall thickness of ½ inch. The cell walls had threaded openings 53 for placement of sensor assemblies 54 and thermocouple 55. The chamber was designed to withstand pressures up to 2500 psi. The sensor had inlet port 56 and outlet port 57 for the recirculation of the aqueous solution in which the $P_{O_2}$ and pH was varied. The vessel was heated by insulated heating tapes from Omega Engineering Co. (not shown) K-Type thermocouples from Omega Engineering Co. were used to measure the temperature. The thermocouples were fixed with Swagelok® fittings to prevent any leaks at high pressures. The measurements were carried out at three different temperatures: 70° C., 120° C. and 180° C. The pressure during the experiments was maintained at 300 psi.

Each sensor tested in the sensor chamber 41 had the basic configuration shown in FIG. 1.

Three different sensor assemblies were studied to determine the contributions of pH, temperature and $P_{O_2}$ to the observed emf. The three different sensor assemblies were:

(I) Chromel contact wire, Hg/HgO|La$_{0.95}$Sr$_{0.05}$F$_{2.95}$+5 mole % La$_2$O$_3$|Pt paste, test solution, Pt contact wire (II) Chromel contact wire, Ag/Ag$_2$O|La$_{0.95}$Sr$_{0.05}$F$_{2.95}$+5 mole % La$_2$O$_3$|Pt paste, test solution, Pt contact wire (III) Chromel contact wire, Ti/TiH$_2$|La$_{0.95}$Sr$_{0.05}$F$_{2.95}$|Pt paste, test solution, Pt contact wire Each assembly was studied for the contribution of each factor, e.g. pH, temperature and $P_{O_2}$, to the observed emf by holding two of the factors constant and observing the emf response to changes in the third factor, e.g. holding the temperature and pH of the contacted medium constant and observing the change in emf in response to changes in the oxygen concentration of the solution. Based on the observed results, the following equations were derived for each sensor. The equations relate the observed emf to the contribution from pH, temperature and $P_{O_2}$ for the aqueous mediums which fall within the following parameters: (T= 70° to 180° C.; $P_{O_2}$=1–0.002; pH= 9.18.

For sensor (I), the equation is:

$$\text{emf} = -20.80 \log (P_{O_2}) + 65.95 \text{ pH} - 0.82T - 80$$

For sensor (II), the equation is:

$$\text{emf} = -23.55 \log (P_{O_2}) + 33.21 \text{ pH} - 1.06T + 575$$

For sensor (III), the equation is:

$$\text{emf} = -43.07 \log (P_{O_2}) + 183.11 \text{ pH} - 2.22T - 850$$

Since the above sensors provide different emfs based on the same pH and oxygen concentration of an aqueous medium, any two of the above sensors can be used in conjunction to determine the pH and oxygen concentration of an aqueous medium, where both values are unknown. To determine the unknown pH and oxygen concentration, Sensor I and Sensor III may be contacted with a solution. If the temperature of the solution is known, e.g. by measuring with a thermocouple, after measuring the emf for each sensor, one obtains two equations with two unknowns. By solving the equations, one may obtain both the pH and the oxygen concentration of the aqueous medium.

It is evident from the above results that improved sensors comprising fluoride based, solid-state electrolytes can be used to successfully determine the pH and/or oxygen concentration of an aqueous medium. The fluoride electrolyte of the subject sensors is physically and chemically stable in that it: (a) does not chemically react with water; (b) exhibits a stable conductivity; and has a constant surface morphology over the working environment in which it is employed. The fluoride electrolyte has a high conductivity over temperatures ranging from 50° to 350° C. Furthermore, the conductivity of the electrolyte is 4 to 5 magnitudes greater than that of comparable Zirconia based electrolytes over this temperature range. Because the subject sensors are sensitive to both the pH and oxygen concentration of an aqueous medium at temperatures ranging from 50° to 350° C. at high pressures, they may be used to determine the pH and oxygen concentration of an aqueous medium in situ, thereby providing a significant advance over known sensors used to measure the pH and oxygen concentration, such as sensors used to measure the corrosion potentials of aqueous mediums in coolant systems.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for detecting the pH of an aqueous medium, said method comprising:

contacting an aqueous medium with an electrochemical sensor comprising a closed-end cylinder shaped fluoride based solid-state electrolyte having an inner and outer surface and an internal reference electrode in contact with said inner surface, where in said contacting step, said aqueous medium is contacted with said outer surface of said electrolyte;

measuring the resultant emf across said electrolyte; and determining the pH of said aqueous medium from said measured emf.

2. The method according to claim 1, wherein said fluoride based electrolyte is described by the formula:

$$La_\alpha X_\beta F_\lambda$$

where α ranges from 0.95 to 1.0;

X is an alkaline earth metal selected from group consisting of Ba, Sr, Ca;

β ranges from 0.0 to 0.05; and

λ ranges from 2.95 to 3.0.

3. The method according to claim 1, wherein said internal reference electrode comprises a hydride.

4. A method for detecting the pH and oxygen concentration of an aqueous medium, said method comprising:

contacting an aqueous medium with a first and second electrochemical sensor, wherein said first and second sensors comprise a closed-end cylinder shaped fluoride based solid-state electrolyte having an inner and outer surface and an internal reference electrode in contact with said inner surface, wherein said first and second internal reference electrodes are different, where in said contacting step, said aqueous medium is contacted with said outer surfaces of said electrolytes of said first and second sensors;

measuring the resultant emf across said electrolytes of said first and second sensors; and determining the pH and oxygen concentration of said aqueous medium from said measured emfs.

5. The method according to claim 4, wherein said internal reference electrode of said first sensor comprises a hydride.

6. The method according to claim 5, wherein said hydride is $Ti/TiH_2$.

7. The method according to claim 4, wherein said electrolyte of said second sensor is doped with a doping oxide and said internal reference electrode comprises an oxide.

8. The method according to claim 7, wherein said internal reference electrode is selected from $Ag/Ag_2O$ or $Hg/HgO$.

9. A sensor device for use in the simultaneous detection of the pH and oxygen concentration of an aqueous medium, said device comprising:

a first and second sensor, wherein said first and second sensors comprise a fluoride based solid state electrolyte having a first major surface and second major surface, said second major surface in contact with an internal reference electrode, wherein said internal reference electrode of said first sensor is a hydride and said internal reference electrode of said second sensor is an oxide.

10. The sensor device according to claim 9, wherein said fluoride based electrolyte is described by the formula:

$$La_\alpha X_\beta F_{80}$$ 

wherein:

α ranges from 0.95 to 1.0;

X is an alkaline earth metal selected from the group consisting of Ba, Sr and Ca;

β ranges from 0.0 to 0.05; and

λ ranges from 2.95 to 3.0.

11. The sensor device according to claim 9, wherein said electrolyte of said second sensor is doped with an oxide.

12. The sensor device according to claim 9, wherein said electrolyte of said first and second sensors is a closed end cylinder, wherein the inner surface of said cylinder is said second major surface and the outer surface of said cylinder is said first major surface.

13. A method for detecting the pH and oxygen concentration of an aqueous medium, said method comprising:

contacting an aqueous medium with the sensor according to claim 9, where in said contacting step said aqueous medium is contacted with said first major surfaces of said electrolytes of said first and second sensors;

measuring the resultant emf across said electrolytes of said first and second sensors; and determining the pH and oxygen concentration of said aqueous medium from said measured emfs.

14. A sensor device for use in the simultaneous detection of the pH and oxygen concentration of an aqueous medium, said device comprising:

first and second sensors, wherein said first and second sensors comprise a fluoride based solid state electrolyte of the formula $La_{0.95}X_{0.05}F_{2.95}$, wherein X is selected from the group consisting of Ba and Sr, said solid state electrolyte having a first major surface and second major surface, said second major surface in contact with an internal reference electrode, wherein said internal reference electrode of said first sensor is a hydride and said internal reference electrode of said second sensor is an oxide, wherein said electrolyte of said second sensor is doped with an oxide.

15. The sensor device according to claim 14, wherein said electrolyte of said second sensor is doped with $La_2O_3$.

16. The sensor device according to claim 14, wherein said oxide reference electrode of said second sensor is selected from the group consisting of $Ag/Ag_2O$ and $Hg/HgO$.

17. The sensor device according to claim 14, wherein said hydride reference electrode is $Ti/TiH_2$.

18. A method for detecting the pH and oxygen concentration of an aqueous medium, said method comprising:

contacting an aqueous medium with the sensor device according to claim 14, where in said contacting step said aqueous medium is contacted with said first major surfaces of said electrolytes of said first and second sensors;

measuring the resultant emf across said electrolytes of said first and second sensors; and determining the pH and oxygen concentration of said aqueous medium from said measured emfs.

* * * * *